US012521475B2

(12) United States Patent
Chen et al.

(10) Patent No.: US 12,521,475 B2
(45) Date of Patent: Jan. 13, 2026

(54) METHOD, DEVICE, AND PRODUCT FOR TREATING A BODY FLUID OF A PATIENT WITH AN INFLAMMATORY CYTOKINE STORM BY BINDING AN ANTIBODY TO A CYTOKINE ANTIGEN IN THE BODY FLUID TO FORM AN ANTIGEN-ANTIBODY COMPLEX THAT IS REMOVED FROM THE BODY FLUID TO REDUCE THE AMOUNT OF THE CYTOKINES IN THE BODY FLUID

(71) Applicants: Arizona Board of Regents on Behalf of Arizona State University, Scottsdale, AZ (US); Marv Enterprises LLC, Hermitage, PA (US)

(72) Inventors: Qiang Chen, Chandler, AZ (US); Collin Bradley Jugler, Mesa, AZ (US); Haiyan Sun, Chandler, AZ (US); Adrian Esqueda, Tempe, AZ (US); Mitchell S. Felder, Hermitage, PA (US)

(73) Assignees: Arizona Board of Regents on Behalf of Arizona State University, Scottsdale, AZ (US); Marv Enterprises LLC, Hermitage, PA (US)

( * ) Notice: Subject to any disclaimer, the term of this patent is extended or adjusted under 35 U.S.C. 154(b) by 708 days.

(21) Appl. No.: 17/917,592

(22) PCT Filed: Apr. 8, 2021

(86) PCT No.: PCT/US2021/026386

§ 371 (c)(1),
(2) Date: Oct. 7, 2022

(87) PCT Pub. No.: WO2021/207497

PCT Pub. Date: Oct. 14, 2021

(65) Prior Publication Data

US 2023/0148395 A1 May 11, 2023

Related U.S. Application Data

(60) Provisional application No. 63/007,207, filed on Apr. 8, 2020.

(51) Int. Cl.
*A61M 1/34* (2006.01)
*A61M 1/36* (2006.01)

(52) U.S. Cl.
CPC ........ *A61M 1/3486* (2014.02); *A61M 1/3496* (2013.01); *A61M 1/3621* (2013.01)

(58) Field of Classification Search
CPC . A61M 1/3486; A61M 1/3496; A61M 1/3621
See application file for complete search history.

(56) References Cited

U.S. PATENT DOCUMENTS 10,925,889 B2 * 2/2021 Peyman ............... A61K 31/513
2005/0271653 A1 * 12/2005 Strahilevitz ........ C07K 16/3053
424/140.1

(Continued)

FOREIGN PATENT DOCUMENTS

WO WO-2015171270 A1 * 11/2015 ............ A61M 1/362

OTHER PUBLICATIONS

ISA/EP, European Patent Office, International Search Report, Jul. 29, 2021, 4 pages, European Patent Office.

*Primary Examiner* — Guy K Townsend

(57) ABSTRACT

An embodiment provides a method for treating a body fluid of a patient with an inflammatory cytokine storm, including: removing the body fluid from a patient; applying a treatment to the body fluid, wherein the treatment comprises an antibody that joins with an antigen in the body fluid to form an antibody-antigen complex; removing the antibody-anti- (Continued)

gen complex from the body fluid; and returning the body fluid to the patient. Other aspects are described and claimed.

14 Claims, 3 Drawing Sheets

Specification includes a Sequence Listing.

(56) References Cited

U.S. PATENT DOCUMENTS

2011/0250287 A1* 10/2011 Bristow .................... A61P 3/06
424/529
2012/0323158 A1* 12/2012 Tebbey ................. A61M 1/362
604/6.01
2015/0071935 A1* 3/2015 Felder .................. C07K 16/248
424/140.1
2015/0283318 A1* 10/2015 Wang .................. A61M 1/3679
600/1
2017/0065717 A1* 3/2017 Felder ................ A61K 39/3955
2018/0161410 A1* 6/2018 Wang ................... A61K 39/385
2020/0171232 A1* 6/2020 McAlvin ............. A61M 1/3618
2022/0362450 A1* 11/2022 Langenegger ...... A61M 1/3486
2023/0148395 A1* 5/2023 Chen ................... A61M 1/3621
604/6.01
2023/0173155 A1* 6/2023 Natuzzi ............... A61M 1/3493
210/646
2023/0218811 A1* 7/2023 Jalan ....................... A61M 1/34
604/5.04
2023/0248684 A1* 8/2023 Chang .................... A61K 45/06
514/510

* cited by examiner

SEQUENCE LISTING

```
<160> NUMBER OF SEQ ID NOS: 8

<210> SEQ ID NO 1
<211> LENGTH: 355
<212> TYPE: DNA
<213> ORGANISM: Mus musculus

<400> SEQUENCE: 1

caagtacagc tgcaggagtc tggacctgag ctggtgaagc ctggggcttt agtgaagata      60

tcctgcaagg cttctggtta caccttcaca acctacgata taaactggat gaagcagagg     120

cctggacagg gacttgagtg gattggatgg atttatcctg gagatgggag tacaaagtac     180

aatgagaaat tcaggggcaa ggtcacactg actgcagaca aatcctccaa cacagtctac     240

atgcacctca tcagcctgcc ttctgagaag tctgcagtct atttctgtgc aagatcggtc     300

ctgggacggg ggtttactta ctggggccaa gggactctgg tcactgtctc tgcag          355


<210> SEQ ID NO 2
<211> LENGTH: 118
<212> TYPE: PRT
<213> ORGANISM: Mus musculus

<400> SEQUENCE: 2

Gln Val Gln Leu Gln Glu Ser Gly Pro Glu Leu Val Lys Pro Gly Ala
1               5                   10                  15

Leu Val Lys Ile Ser Cys Lys Ala Ser Gly Tyr Thr Phe Thr Thr Tyr
            20                  25                  30

Asp Ile Asn Trp Met Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Arg Gly Lys Val Thr Leu Thr Ala Asp Lys Ser Ser Asn Thr Val Tyr
65                  70                  75                  80

Met His Leu Ile Ser Leu Pro Ser Glu Lys Ser Ala Val Tyr Phe Cys
                85                  90                  95

Ala Arg Ser Val Leu Gly Arg Gly Phe Thr Tyr Trp Gly Gln Gly Thr
            100                 105                 110

Leu Val Thr Val Ser Ala
        115


<210> SEQ ID NO 3
<211> LENGTH: 334
<212> TYPE: DNA
<213> ORGANISM: Mus musculus

<400> SEQUENCE: 3

gacattgtga tgacacagac tccagcttct ttggctgtgt ctctagggca gagggccacc      60

atatcctgca gagccagtga aagtgttgat agttatggca atagttttat gcactggtac     120

cagcagaaac caggacagcc acccaaagtc ctcatctatt ttgcatccaa cctagaatct     180

ggggtccctg ccaggttcag tggcagtggg tctaggacag acttcaccct caccattgat     240

cctgtggagg ctgatgatgc tgcaacctat tactgtcagc aaaataatga ggatccatac     300
```

acgttcggag gggggaccaa gctggaaata aaac 334

<210> SEQ ID NO 4
<211> LENGTH: 111
<212> TYPE: PRT
<213> ORGANISM: Mus musculus

<400> SEQUENCE: 4

Asp Ile Val Met Thr Gln Thr Pro Ala Ser Leu Ala Val Ser Leu Gly
1 5 10 15

Gln Arg Ala Thr Ile Ser Cys Arg Ala Ser Glu Ser Val Asp Ser Tyr
20 25 30

Gly Asn Ser Phe Met His Trp Tyr Gln Gln Lys Pro Gly Gln Pro Pro
35 40 45

Lys Val Leu Ile Tyr Phe Ala Ser Asn Leu Glu Ser Gly Val Pro Ala
50 55 60

Arg Phe Ser Gly Ser Gly Ser Arg Thr Asp Phe Thr Leu Thr Ile Asp
65 70 75 80

Pro Val Glu Ala Asp Asp Ala Ala Thr Tyr Tyr Cys Gln Gln Asn Asn
85 90 95

Glu Asp Pro Tyr Thr Phe Gly Gly Gly Thr Lys Leu Glu Ile Lys
100 105 110

<210> SEQ ID NO 5
<211> LENGTH: 354
<212> TYPE: DNA
<213> ORGANISM: Mus musculus

<400> SEQUENCE: 5
caagtgcagc tggaggagtc tggacctgag ctggtgaagc ctggggcttt agtgaagata 60
tcctgcaagg cttctggtta caccttcaca agctacgata taaactggat gaagcagagg 120
cctggacagg gacttgagtg gattggatgg atttatcctg gagatggtag tactaagtac 180
aatgagaaat tcaagggcaa ggccacactg actgcagaca aatcctccag cacagcctac 240
atgcagatca gtagcctgac ttctgaaaac tctgcagtct atttctgtgc aagatccgac 300
ttcggccacg ggtttgttta ctggggccaa gggactctgg tcactgtctc tgca 354

<210> SEQ ID NO 6
<211> LENGTH: 118
<212> TYPE: PRT
<213> ORGANISM: Mus musculus

<400> SEQUENCE: 6

Gln Val Gln Leu Glu Glu Ser Gly Pro Glu Leu Val Lys Pro Gly Ala
1 5 10 15

Leu Val Lys Ile Ser Cys Lys Ala Ser Gly Tyr Thr Phe Thr Ser Tyr
20 25 30

Asp Ile Asn Trp Met Lys Gln Arg Pro Gly Gln Gly Leu Glu Trp Ile
35 40 45

Gly Trp Ile Tyr Pro Gly Asp Gly Ser Thr Lys Tyr Asn Glu Lys Phe
50 55 60

Lys Gly Lys Ala Thr Leu Thr Ala Asp Lys Ser Ser Ser Thr Ala Tyr
65 70 75 80

Met Gln Ile Ser Ser Leu Thr Ser Glu Asn Ser Ala Val Tyr Phe Cys
85 90 95

Ala Arg Ser Asp Phe Gly His Gly Phe Val Tyr Trp Gly Gln Gly Thr

-continued

```
            100                 105                 110

Leu Val Thr Val Ser Ala
        115


<210> SEQ ID NO 7
<211> LENGTH: 334
<212> TYPE: DNA
<213> ORGANISM: Mus musculus

<400> SEQUENCE: 7

gatattgtgc tcacacagtc tccagcttct ttggctgtgt ctctagggca gagggccacc      60

atatcctgca gagccagtga aagtgttgat acttatgaca atagttttat gcactggtac     120

cagcagaaac caggacagcc acccaaactc ctcatctatc ttgcatccaa cctagaatct     180

ggggtccctg ccaggttcag tggcagtggg tctaggacag acttcaccct caccattgat     240

cctgtggagg ctgatgatgc tgcaatctat tactgtcagc aaaattatga ggatccgtac     300

acgttcggag gggggaccaa gctggaaata aaac                                 334


<210> SEQ ID NO 8
<211> LENGTH: 111
<212> TYPE: PRT
<213> ORGANISM: Mus musculus

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30

Asp Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Ile Tyr Tyr Cys Gln Gln Asn Tyr
                85                  90                  95

Glu Asp Pro Tyr Thr Phe Gly Gly Gly Thr Lys Leu Glu Ile Lys
            100                 105                 110
```

METHOD, DEVICE, AND PRODUCT FOR TREATING A BODY FLUID OF A PATIENT WITH AN INFLAMMATORY CYTOKINE STORM BY BINDING AN ANTIBODY TO A CYTOKINE ANTIGEN IN THE BODY FLUID TO FORM AN ANTIGEN-ANTIBODY COMPLEX THAT IS REMOVED FROM THE BODY FLUID TO REDUCE THE AMOUNT OF THE CYTOKINES IN THE BODY FLUID

CROSS REFERENCE TO RELATED APPLICATION

This application claims priority to U.S. Provisional Patent Application Ser. No. 63/007,207, filed on Apr. 8, 2020, and entitled "METHOD FOR TREATING COVID-19 INFLAMMATORY CYTOKINE STORM FOR THE REDUCTION OF MORBIDITY AND MORTALITY IN COVID-19 PATIENTS," the contents of which are incorporated by reference herein.

FIELD

This application relates generally to a treatment for Covid-19, and, more particularly, to an extracorporeal methodology for the treatment of Covid-19.

BACKGROUND

Coronaviruses are a family of viruses that can cause illnesses such as severe acute respiratory syndrome (SARS) and Middle East respiratory syndrome (MERS). A new coronavirus (Covid-19) was identified as the cause of a disease outbreak in China. The virus is known as the severe acute respiratory syndrome coronavirus 2 (SARS-CoV-2). The disease it causes is called coronavirus disease 2019 (COVID-19).

Cases of COVID-19 have been reported in multiple countries, where it has caused a great deal of morbidity and mortality, in a worldwide pandemic. The disorder is characterized by shortness of breath, increased mucus production, sore throat, cough, and fever. This may necessitate admission to a hospital, with subsequent admission to an intensive care unit for the respiratory support of the infected patient. The etiology for admission to an intensive care unit in Covid-19 patients is mainly due to the overproduction of inflammatory cytokines, which subsequently causes an overwhelming production of edema and mucus in the lungs bilaterally. This overwhelming production of edema and mucus causes morbidity and mortality by decreasing oxygenation of the lung tissue to critical levels.

There is a need for treatments to reduce the Covid-19 inflammatory cytokine storm in patients, resulting in less respiratory and other pathologies in those patients, resulting in less morbidity and mortality.

BRIEF SUMMARY

In summary, one embodiment provides a method for treating a body fluid of a patient with an inflammatory cytokine storm, comprising: removing the body fluid from a patient; applying a treatment to the body fluid, wherein the treatment comprises an antibody that joins with an antigen in the body fluid to form an antibody-antigen complex; removing the antibody-antigen complex from the body fluid; and returning the body fluid to the patient.

Another embodiment provides a device for treating a body fluid extracorporeally of a patient with an inflammatory cytokine storm, comprising: a first stage including an inlet for the body fluid and at least one exterior wall defining a treatment chamber; a second stage, fluidly connected to the first stage, comprising a removal module and an outlet for the body fluid, wherein the treatment chamber comprises a delivery tube for introducing a treatment into the treatment chamber, wherein the delivery tube comprises a hollow tube including at least one interior wall defining a plurality of holes through which the treatment can be added to the treatment chamber, wherein the treatment is delivered through the hollow tube in counter-current mode with reference to the body fluid; the device being configured to: remove the body fluid from a patient; apply a treatment to the body fluid, wherein the treatment comprises an antibody that joins with an antigen in the body fluid to form an antibody-antigen complex; remove the antibody-antigen complex from the body fluid; and return the body fluid to the patient.

A further embodiment provides a product for treating a body fluid extracorporeally of a patient with an inflammatory cytokine storm, comprising: a first stage including an inlet for the body fluid and at least one exterior wall defining a treatment chamber; a second stage, fluidly connected to the first stage, comprising a removal module and an outlet for the body fluid, wherein the treatment chamber comprises a delivery tube for introducing a treatment into the treatment chamber, wherein the delivery tube comprises a hollow tube including at least one interior wall defining a plurality of holes through which the treatment can be added to the treatment chamber, wherein the treatment is delivered through the hollow tube in counter-current mode with reference to the body fluid.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
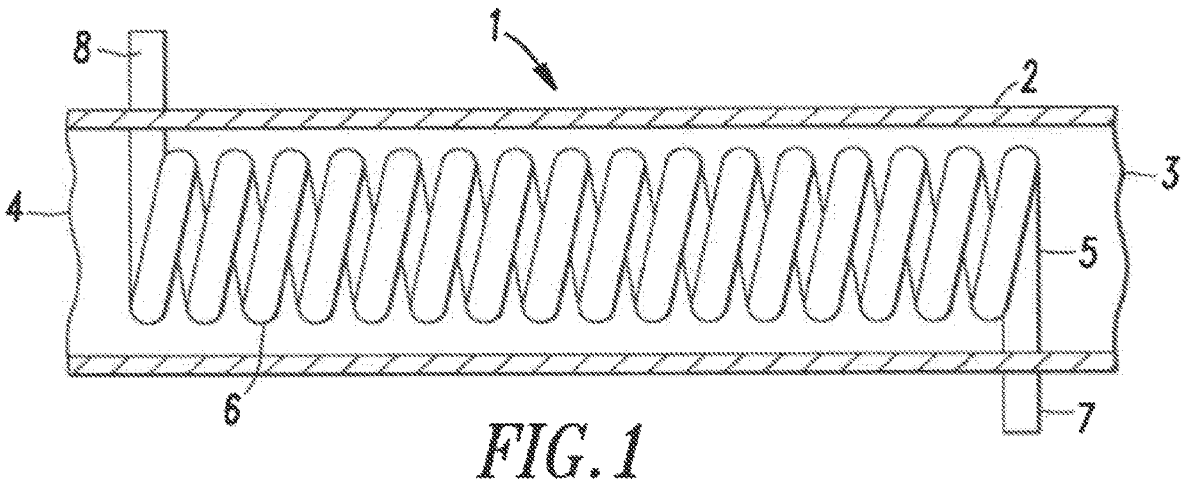
FIG. 1 illustrates an example partial cross-sectional view of a cylinder and tubing used to deliver a treatment to a bodily fluid.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

COVID-19 has spread worldwide and become a global pandemic. The loss of life, suffering, and economic struggles have reached all corners of the globe. Symptoms may manifest about 2-14 days after exposure. The symptoms may include fever, chills, cough, shortness of breath, difficulty breathing, fatigue, muscle/body aches, new loss of taste/smell, sore throat, congestion, runny nose, nausea, vomiting, or diarrhea. More severe symptoms may include trouble breathing, persistent pain/pressure in the chest, confusion, inability to wake or stay awake, or bluish lips/face. Some cases may require hospitalization and even intensive care unit healthcare. Because of the novelty of the virus, very few tests exist that are specific for COVID-19. What is needed is a treatment of COVID-19 in a patient.

Coronaviruses are a family of viruses that can cause illnesses such as severe acute respiratory syndrome (SARS) and Middle East respiratory syndrome (MERS). A new coronavirus (Covid-19) was identified as the cause of a disease outbreak in China. The virus is known as the severe acute respiratory syndrome coronavirus 2 (SARS-CoV-2). The disease it causes is called coronavirus disease 2019 (COVID-19).

In a phylogenetic analysis of 103 strains of SARS-CoV-2 from China, two different types of SARS-CoV-2 were identified, designated type L (accounting for 70 percent of the strains) and type S (accounting for 30 percent). The strains in L type, derived from S type, are evolutionarily more aggressive and contagious.

Cases of COVID-19 have been reported in multiple countries, where it has caused a great deal of morbidity and mortality, in a worldwide pandemic. The disorder is characterized by shortness of breath, increased mucus production, sore throat, cough, and fever. This may necessitate admission to a hospital, with subsequent admission to an intensive care unit for the respiratory support of the infected patient. There is therefore a need for treatments to reduce Covid-19 symptomatology in a clinical setting.

Accordingly, a method of extracorporeal treating a patient's body fluid, for example, blood, and/or CSF (cerebrospinal fluid) to decrease the cytokine storm caused by a severe acute respiratory syndrome coronavirus 2 (SARS-CoV-2) infection resulting in Covid-19 disease (herein following referred to as "Covid-19") is disclosed. In the first stage of the treatment, the body fluid (blood and/or CSF) is removed from the Covid-19 patient. Several methods of a second stage of treatment include applying antibodies directed to an antigen or multiple antigens associated with the cytokine storm (Covid-19 TA(s)) to the body fluid (blood and/or CSF) forming antibody-antigen complexes and then using removing the antibody-antigen complexes from the body fluid. Various alternative method for removing the antibody-antigen complexes are disclosed. These antibody treatment methods may include using primary antibodies against Covid-19 TA(s) conjugated to alternative moieties to effectuate removal of the complexes. Alternative methods comprise using non-conjugated primary antibodies along with conjugated (with alternative moieties) secondary antibodies to effectuate removal of complexes. Alternative methods that may not require the use of antibodies for the removal of the Covid-19 TA(s) are also disclosed. The third stage of treatment comprises returning the body fluid to the patient.

The severe symptoms seen in Covid-19 patients may result from the cytokine storm produced by immune system reacting to the presence of the virus. What is needed is a method to mitigate and reduce the cytokine storm seen in these patients. Several methods comprise treating a patient's body fluid extracorporeally with antibody(s) designed to react with particular Covid-19 TA(s), which include but are not limited to: IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemoattractant protein 1), MIP1A (Macrophage inflammatory protein-1-alpha), TNF-alpha (Tumor necrosis factor-alpha) (herein all collectively are referred to as Covid-19 TA(s)), removing the antibody antigen complexes that are formed in methods where that is necessary, and then returning the cleansed body fluid back to the Covid-19 patient.

In the first stage, body fluid is removed from a Covid-19 patient. A non-limiting example of a method for removing blood includes using standard venipuncture technique. A non-limiting example of a method for removing the CSF is by using standard lumbar puncture technique. In a non-limiting example for treating blood of a Covid-19 patient, 25 ml to 500 ml of blood is removed from a patient by a catheter, the extracorporeal blood is exposed to antibodies generated against antigens associated with the cytokine storm (Covid-19 TA(s). For a non-limiting example of how a body fluid can be exposed antibodies, as illustrated in the device described in FIG. 1 and FIG. 2. The antibody/antigen complexes formed after exposure can then be removed by various methods described more in detail below. The cleansed blood can then be returned to the patient, for (a non-limiting) example by using the same catheter that was originally used in removing the blood. The frequency of such treatments would depend upon an analysis of the underlying symptomatology and pathology of the patient.

In an embodiment, the antibodies listed below may be used, which are appended hereto:

Antibody B16, Mus musculus VH nucleotide sequence:

```
CAAGTACAGCTGCAGGAGTCTGGACCTGAGCTGGTGAAGCCTGGGGCTTT
AGTGAAGATATCCTGCAAGGCTTCTGGTTACACCTTCACAACCTACGATA
TAAACTGGATGAAGCAGAGGCCTGGACAGGGACTTGAGTGGATTGGATGG
ATTTATCCTGGAGATGGGAGTACAAAGTACAATGAGAAATTCAGGGGCAA
```

-continued

GGTCACACTGACTGCAGACAAATCCTCCAACACAGTCTACATGCACCTCA

TCAGCCTGCCTTCTGAGAAGTCTGCAGTCTATTTCTGTGCAAGATCGGTC

CTGGGACGGGGGTTTACTTACTGGGGCCAAGGGACTCTGGTCACTGTCTC

TGCAG, with an ammo acid sequence:

QVQLQESGPELVKPGALVKISCKASGYTFTTYDINWMKQRPGQGLEWIGW

IYPGDGSTKYNEKFRGKVTLTADKSSNTVYMHLISLPSEKSAVYFCARSV

LGRGFTYWGQGTLVTVSA.

Antibody B16, Mus musculus VL nucleotide sequence:

GACATTGTGATGACACAGACTCCAGCTTCTTTGGCTGTGTCTCTAGGGCA

GAGGGCCACCATATCCTGCAGAGCCAGTGAAAGTGTTGATAGTTATGGCA

ATAGTTTTATGCACTGGTACCAGCAGAAACCAGGACAGCCACCCAAAGTC

CTCATCTATTTTGCATCCAACCTAGAATCTGGGGTCCCTGCCAGGTTCAG

TGGCAGTGGGTCTAGGACAGACTTCACCCTCACCATTGATCCTGTGGAGG

CTGATGATGCTGCAACCTATTACTGTCAGCAAAATAATGAGGATCCATAC

ACGTTCGGAGGGGGGACCAAGCTGGAAATAAAAC, with an amino acid sequence:

DIVMTQTPASLAVSLGQRATISCRASESVDSYGNSFMHWYQQKPGQPPKV

LIYFASNLESGVPARFSGSGSRTDFTLTIDPVEADDAATYYCQQNNEDPY

TFGGGTKLEIK.

Antibody N12, Mus musculus VH nucleotide sequence:

CAAGTGCAGCTGGAGGAGTCTGGACCTGAGCTGGTGAAGCCTGGGGCTTT

AGTGAAGATATCCTGCAAGGCTTCTGGTTACACCTTCACAAGCTACGATA

TAAACTGGATGAAGCAGAGGCCTGGACAGGGACTTGAGTGGATTGGATGG

ATTTATCCTGGAGATGGTAGTACTAAGTACAATGAGAAATTCAAGGGCAA

GGCCACACTGACTGCAGACAAATCCTCCAGCACAGCCTACATGCAGATCA

GTAGCCTGACTTCTGAAAACTCTGCAGTCTATTTCTGTGCAAGATCCGAC

TTCGGCCACGGGTTTGTTTACTGGGGCCAAGGGACTCTGGTCACTGTCTC

TGCA, with an ammo acid sequence:

QVQLEESGPELVKPGALVKISCKASGYTFTSYDINWMKQRPGQGLEWIGW

IYPGDGSTKYNEKFKGKATLTADKSSSTAYMQISSLTSENSAVYFCARSD

FGHGFVYWGQGTLVTVSA.

Antibody N12, Mus musculus VL nucleotide sequence:

GATATTGTGCTCACACAGTCTCCAGCTTCTTTGGCTGTGTCTCTAGGGCA

GAGGGCCACCATATCCTGCAGAGCCAGTGAAAGTGTTGATACTTATGACA

ATAGTTTTATGCACTGGTACCAGCAGAAACCAGGACAGCCACCCAAACTC

CTCATCTATCTTGCATCCAACCTAGAATCTGGGGTCCCTGCCAGGTTCAG

-continued

TGGCAGTGGGTCTAGGACAGACTTCACCCTCACCATTGATCCTGTGGAGG

CTGATGATGCTGCAATCTATTACTGTCAGCAAAATTATGAGGATCCGTAC

ACGTTCGGAGGGGGGACCAAGCTGGAAATAAAAC, with an ammo acid sequence:

DIVLTQSPASLAVSLGQRATISCRASESVDTYDNSFMHWYQQKPGQPPKL

LIYLASNLESGVPARFSGSGSRTDFTLTIDPVEADDAAIYYCQQNYEDPY

TFGGGTKLEIK.

The Covid-19/TA(s) such as IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemo attractant protein 1), MIP1A (Macrophage inflammatory protein-1-alpha), and TNF-alpha (Tumor necrosis factor-alpha) can be identified and differentiated using standard ELISA methodology. Identification can be done before treatment to determine which Covid-19 TA(s) are present in patient's blood and after treatment to analyze the efficiency of removal of the Covid-19 TA(s). One non-limiting method is the ELISA (enzyme-linked immunosorbant assay) method. ELISA is a biochemical technique which allows for the detection of an antigen in a sample of blood as a non-limiting example. In ELISA, an antigen is affixed to a surface, and then an antibody is utilized for binding to the antigen. The antibody is linked to an enzyme which enables a color change in the substrate. Other strategies may be employed to validate the level of target antigen(s)/TA(s) in the body fluid before or after treatment: Western blotting technology, UV/Vis spectroscopy, mass spectrometry, and surface plasmon resonance (SPR).

To increase the effectiveness of the treatment of the body fluid, the antibodies selected for use against the Covid-19 TA(s) may be conjugated with a moiety. In one embodiment, the antibody selected is conjugated to an albumin moiety wherein dialysis is used to remove the albumin-antibody-antigen complex. Various dialysis methods are known by one skilled in the art are contemplated in this disclosure and are described in more detail below. An alternative embodiment utilizes an antibody conjugated to a macromolecular moiety instead of an albumin moiety. The macromolecular moiety is preferably between 1.000 mm to 0.00001 mm in diameter. The antibody-macromolecular moiety-targeted antigen complex would then be blocked from reentering the patient's blood, by using a series of microscreens which contain openings with a diameter 50.00000% to 99.99999% less than the diameter of the macromolecular moiety. The microscreen opening(s) must have a diameter of at least 25 microns to allow for the passage and return to circulation of the non-pathology-inducing body fluid constituents.

Another alternative moiety methodology comprises removing the Covid-19 TA(s) from the body fluid by using an antibody containing an iron (Fe) moiety. This will then create an Fe-Antibody-Antigen complex. This iron containing complex may then be efficaciously removed using a strong, localized magnetic force field.

Optionally, any of the above described the antibody-antigen complexes can be initially formed with non-conjugated primary antibodies to any of the Covid-19 TA(s). Secondary antibodies conjugated any of the above described moieties can be used to detect and bind the primary antibody-antigen complexes. These secondary antibody-primary antibody-antigen complexes are then removed, and the purified body fluid is then returned to the patient. Use of a primary and then a secondary antibody may amplify detection of and subsequent removal of the TA(s).

An alternative to using antibodies conjugated to a moiety is to expose the Covid-19 patients body fluid to antibodies attached to microarrays. In a non-limiting example, blood containing one or more of the target antigen(s)/TA(s) IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemoattractant protein 1), MIP1A (Macrophage inflammatory protein-1-alpha), TNF-alpha (Tumor necrosis factor-alpha) is exposed to microarray containing antibodies to an Covid-19 TA(s) of interest, capturing the Covid-19 TA(s). Antibody microarrays are composed of millions of identical monoclonal antibodies attached at high density on glass or plastic slides. After sufficient extracorporeal exposure of the Covid-19 TA(s) to the antibody microarrays, the antibody microarrays-Covid-19 TA(s) may be disposed of, using standard medical practice.

Another alternative to using antibodies conjugated to a moiety is immunoaffinity chromatography. In immunoaffinity chromatography, the heterogeneous group of molecules related to the cytokine storm will be removed from the body fluid by entrapment on a solid or stationary phase or medium containing antibody(s) designed to react with particular Covid-19 TA(s) of the aforementioned cytokines. Only the Covid-19 (TAs) will be trapped using immunoaffinity chromatography, removing them from the body fluid. The solid medium can be removed from the mixture, washed, and the Covid-19 TA(s) may then be released from the entrapment through elution to reuse the immunoaffinity chromatography mediums for continuous treatment.

Another alternative Covid-19 TA(s) removal method is gel filtration chromatography. In gel filtration chromatography, the body fluid is transported through a size exclusion column that will be used to separate the selected Covid-19 TA(s) by size and molecular weight. Yet, another alternative methodology would utilize a molecular weight cut-off filtration. Molecular weight cut-off filtration refers to the molecular weight at which at least 80% of the selected Covid-19 TA(s) is prohibited from membrane diffusion.

Some of the antibody methods described above may utilize a device that comprises two features. The first feature includes an inlet for body fluid and at least one exterior wall defining a treatment chamber that is fluidly connected to a second feature. The second feature comprises a removal module and an outlet for the body fluid. In some embodiments, the removal module is selected from a group comprising a mechanical filter, a chemical filter, a dialysis machine, a molecular filter, molecular adsorbent recirculating system (MARS), a plasmapheresis unit, or combinations thereof.

A non-limiting example of a device that can utilized in the disclosed method comprises a first feature including an inlet for body fluid (blood and/or CSF) and at least one exterior wall defining a treatment chamber that is fluidly connected to a second feature comprising a removal module and an outlet for the body fluid to be treated. The treatment chamber can include a delivery tube for introducing a treatment into the treatment chamber. In embodiments, the delivery tube comprises a hollow tube including at least one interior wall defining a plurality of holes through which the treatment can be added to the treatment chamber. The treatment can also be delivered through the hollow tube in counter-current mode with reference to the flow of the extracorporeal body fluid. The removal module can be any device capable of removing the antibody-antigen complex. In embodiments, the removal module can be selected from a group comprising a mechanical filter, a chemical filter, a dialysis machine, a molecular filter, molecular adsorbent recirculating system (MARS), a plasmapheresis unit, or combinations thereof.

The illustrated example embodiments will be best understood by reference to the figures. The following description is intended only by way of example, and simply illustrates certain example embodiments.

As a non-limiting example shown in FIG. 1, the first feature can include an exterior wall 2 defining a treatment chamber 5. The treatment can be applied in the treatment chamber 5. Residence times of the blood to be treated can be altered by changing the dimensions of the treatment chamber or the flow rate of the body fluid through the treatment chamber 5. Body fluid to be treated enters the inlet 3, passes through the treatment chamber 5, and exits the outlet 4. In embodiments, the antibody treatment can be applied from a delivery tube 6 located within the treatment chamber 5. An interior wall 9 defines the delivery tube 6. The delivery tube 6 can include at least one lead 7, 8. The lead 7, 8 can deliver the antibody treatment to the treatment chamber 5. Conveniently, the delivery tubes 6 will have a high contact surface area with the body fluid. As shown, the delivery tube 6 comprises a helical coil.

Figure 2:
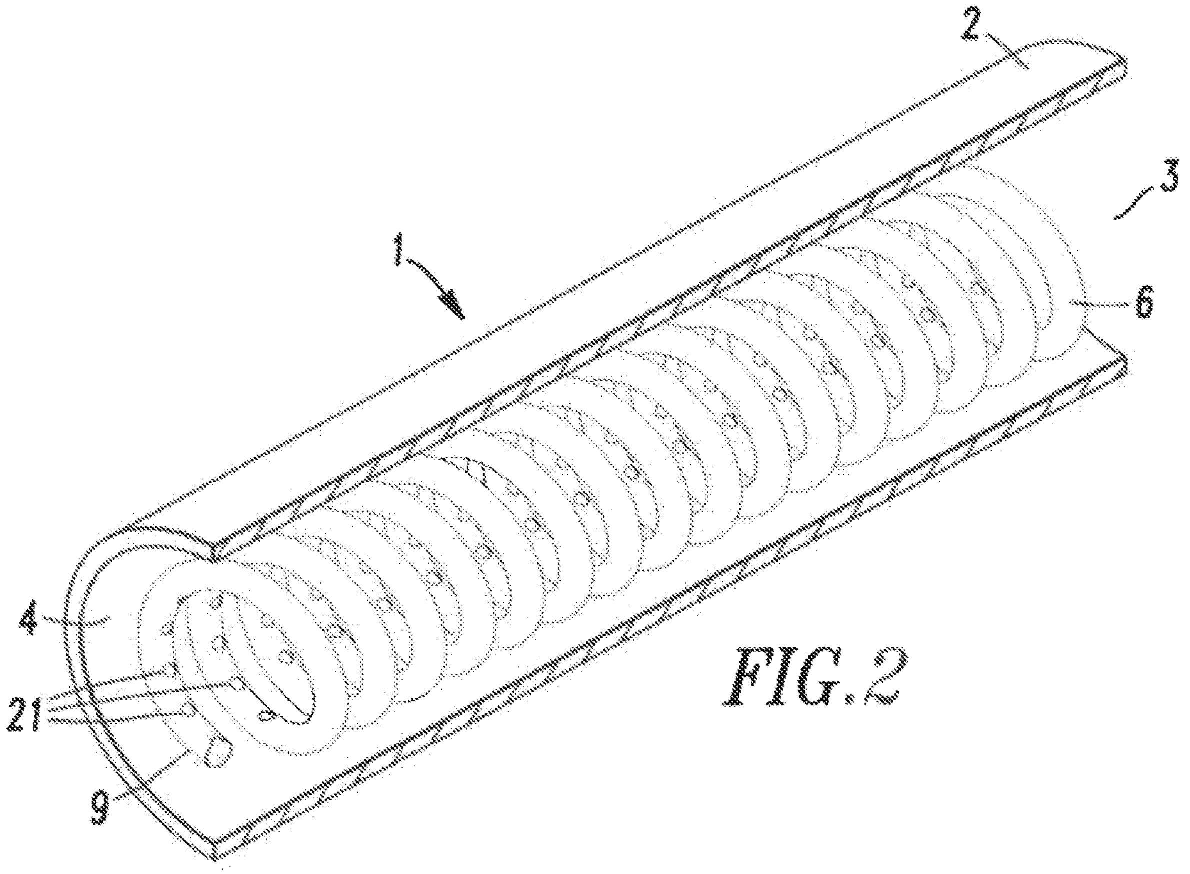
FIG. 2 illustrates an example a partial cross-sectional view showing additional detail of the cylinder and tubing of FIG. 1.

With reference to FIG. 2, the delivery tube 6 can be hollow and the interior wall 9 can define a plurality of holes 21. In this design for example, antibodies can be pumped through the delivery tube 6 to affect a desired concentration of antibodies in the body fluid (blood and/or CSF). The antibodies can perfuse through the holes 21. The delivery tube 6 can include any suitable material including, for example, metal, plastic, ceramic or combinations thereof. The delivery tube 6 can also be rigid or flexible. In one embodiment, the delivery tube 6 is a metal tube perforated with a plurality of holes. Alternatively, the delivery tube 6 can be plastic.

Antibodies targeting the Covid-19 TA(s) can be delivered in a concurrent or counter-current mode with reference to the blood and/or CSF. In counter-current mode, the body fluid enters the treatment chamber 5 at the inlet 3. The selected antibody(s) can enter through a first lead 8 near the outlet 4 of the treatment chamber 5. The body fluid then passes to the outlet 4 and the antibodies pass to the second lead 7 near the inlet 3. The removal module of the second feature substantially removes the antibodies-antigen molecular compound from the blood and/or CSF.

The second feature can include a filter, such as a dialysis machine, which is known to one skilled in the art. The second feature can include a molecular filter. A non-limiting example is molecular adsorbents recirculating system (MARS), which may be compatible and/or synergistic with dialysis equipment. MARS technology can be used to remove small to average sized molecules from the blood and/or CSF. Artificial liver filtration presently uses this technique.

In practice, a portion of the purified body fluid can be tested to ensure a sufficient portion of any of the Covid-19 TA(s): IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemo attractant protein 1), MIP1A (Macrophage inflammatory protein-1-alpha), and TNF-alpha (Tumor necrosis factor-alpha) has been successfully removed from the body fluid using methods discussed throughout this application. Testing after initial treatment can determine the length of treatment and evaluate the efficacy of the any of the removal methodologies disclosed. Body fluid with an unacceptably high concentration of complex remaining can then be re-treated before returning the body fluid to the patient.

In some embodiments, the second stage treating the body fluid to remove the antibody-moiety-targeted antigen complex by may include various techniques such as, but not limited to: filtering based on molecular size, protein binding, solubility, chemical reactivity, and combinations thereof. As a non-limiting example, a filter can include a molecular sieve, such as zeolite, or porous membranes that capture complexes comprising molecules above a certain size. Membranes used for some methods can comprise polyacrylonitrile, polysulfone, polyamides, cellulose, cellulose acetate, polyacrylates, polymethylmethacrylates, or combinations thereof. Increasing the flow rate or diasylate flow rate in some methods can increase the rate of removal of the antibody with an attached moiety targeting the Covid-19 TA(s).

Additional removal methods may include continuous renal replacement therapy (CRRT) which can remove large quantities of filterable molecules from the extracorporeal body fluid. CRRT would be particularly useful for molecular compounds that are not strongly bound to plasma proteins. Categories of CRRT include continuous arteriovenous hemofiltration, continuous venovenous hemofiltration, continuous arteriovenous hemodiafiltration, slow continuous filtration, continuous arteriovenous high-flux hemodialysis, and continuous venovenous high flux hemodialysis.

The sieving coefficient (SC) is the ratio of the molecular concentration in the filtrate to the incoming bodily fluid. A SC close to zero implies that the moiety antibody-targeted antigen complex will not pass through the filter. A filtration rate of 10 ml per minute is generally satisfactory. Other methods of increasing the removability of the moiety-antibody-targeted antigen include the use of temporary acidification of the bodily fluid using organic acids to compete with protein binding sites.

Figure 3:
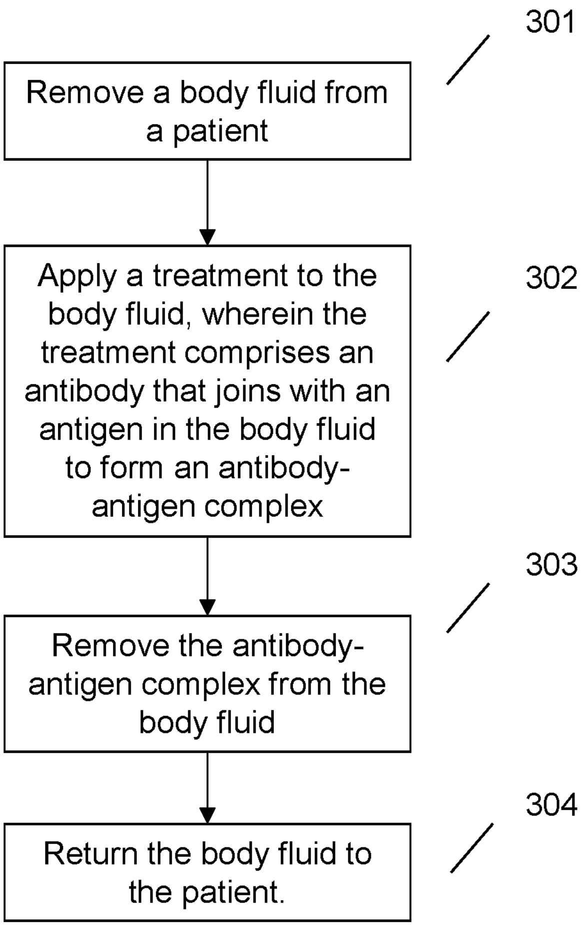
FIG. 3 illustrates an example flow diagram of a method for treatment of Covid-19 using extracorporeal methodology.

Referring to FIG. 3, an example method is illustrated. A method for treating a body fluid comprising: a first stage including removing the body fluid from a patient at 301; a second stage including applying a treatment to the body fluid by introducing an antibody that joins with an antigen in the body fluid to form an antibody-antigen complex at 302, and removing the antibody-antigen complex from the body fluid at 303; and a third stage including returning the body fluid to the patient at 304.

Some embodiments in the context of treating Covid-19 patients as discussed above are outlined below:

A method for treating a body fluid comprising: a first stage including removing the body fluid from a patient; a second stage including applying a treatment to the body fluid and removing the treatment from the body fluid; and a third stage including returning the body fluid to the patient.

A method for treating a body fluid comprising: a first stage including removing the body fluid from a patient; a second stage including applying a treatment to the body fluid by introducing an antibody that joins with an antigen in the body fluid to form an antibody-antigen complex, and removing the antibody-antigen complex from the body fluid; and a third stage including returning the body fluid to the patient.

A method for treating a body fluid comprising: a first stage including removing the body fluid from a patient; a second stage including applying a treatment to the body fluid by introducing an antibody that joins with an antigen in the body fluid to form an antibody-antigen complex, and removing the antibody-antigen complex from the body fluid; wherein the targeted antigen is selected from a group consisting of IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemoattractant protein 1), MIP1A (Macrophage inflammatory protein-1-alpha), and TNF-alpha (Tumor necrosis factor-alpha); and a third stage including returning the body fluid to the patient.

A method for treating a body fluid comprising: a first stage including removing the body fluid from a patient; a second stage including applying a treatment to the body fluid introducing a targeted antibody that joins with an antigen in the body fluid to form an antibody-antigen complex; and conjugating the antibody-antigen complex with a second antibody comprising a moiety that increases the efficacy of removal, thereby forming an antibody-moiety-antigen complex; and a third stage including returning the body fluid to the patient.

A method for treating a body fluid comprising: a first stage including removing the body fluid from a patient; a second stage including applying a treatment to the body fluid by introducing an antibody that joins with an antigen in the body fluid to form an antibody-antigen complex, and removing the complex from the body fluid; wherein the targeted antigen is selected from a group consisting of IL(interleukin)-1alpha, IL-1beta, IL-2, IL-7, IL-10, IL-18, IL-36alpha, IL-36beta, IL-36gamma, IL-33, GM-CSF (Granulocyte-macrophage colony stimulating factor), IP10/CXCL10 (interferon-inducible protein 10), MCP1 (Monocyte chemoattractant protein 1), MIP1A (Macrophage inflammatory protein-1-alpha), TNF-alpha (Tumor necrosis factor-alpha); and a third stage including returning the body fluid to the patient; wherein the method includes determining the efficacy of treatment by testing the body fluid after the treatment and before returning the body fluid to the patient.

In an embodiment, a treatment is applied to a body fluid extracorporeally. The treatment comprises exposing the body fluid to a tagged antibody generated to bind specific targeted pathogenic antigens (TPAs) of the Covid-19 virus, or other target, such as those described above. During this treatment the conjugated antibody(s) and the targeted pathogen antigen form antibody complexes. A method for enhancing radiofrequency (RF) absorption includes providing targeted RF enhancers, such as antibodies with an attached RF absorption enhancer, such as, for example metal particles. The antibodies target and bind to the Covid-19 virion. Binding RF enhancing particles to the antibodies (and other carriers having at least one targeting moiety) permits the injection of the antibodies (and other carriers having at least one targeting moiety) into the extracorporeal target solution. The RF enhancers induce the absorption of energy in the antibody-RF enhancing moiety complex. In addition, a combination of antibodies (and other carriers having at least one targeting moiety bound to different metals (and other RF absorbing particles) can be used allowing for variations in the RF absorption characteristics in the extracorporeal target area. The energy of the emitted radiofrequency (RF) annihilates the antibody-RF enhancing moiety complex, thereby destroying its disease-causing potential. The entire system is monitored and controlled utilizing a computer, in real time, utilizing time units of 1 millisecond or less during the entire procedure. Persons having ordinary skill in art will recognize that the steps described above can be performed on various devices/machines. This disclosure contemplates all known devices/machine that can perform the steps described in the above illustrative example.

A second stage substantially eliminates, through a high-energy radiofrequency emissive source targeting and annihilating, the antibody-RF enhancing moiety complex in the body fluid. A method for killing the Covid-19 virus, or other virus or bacteria, is by introducing into the extracorporeal patient body fluid (blood or CSF) RF absorption enhancers capable of selectively binding to the target virions and further capable of generating sufficient heat to kill or damage the bound target antibody-virion complexes by heat generated solely by the application of an RF field generated by an RF signal between a transmission head and a reception head.

In an embodiment, the methodology described herein may be used to treat other conditions. For example, target antigens may be constructed for many conditions, diseases, infections, or the like. Pathogenic bacteria examples such as, *Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica, Yersinia pseudotuberculosis*, or the like may be treated.

Unless otherwise indicated, all numbers expressing quantities of ingredients, properties such as molecular weight, reaction conditions, and so forth used in the specification and claims are to be understood as being modified in all instances by the term "about."

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

While the invention has been particularly shown and described with reference to a preferred embodiment, it will be understood by those skilled in the art that various changes in form and detail may be made therein without departing from the spirit and scope of the invention. All documents, books, manuals, papers, patents, published patent applications, guides, abstracts, and other references cited herein are incorporated by reference in their entirety.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as an instrument, system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for treating a body fluid of a patient with an inflammatory cytokine storm, comprising:

removing the body fluid from a patient;

applying a treatment to the body fluid, wherein the treatment comprises an antibody that joins with an antigen in the body fluid to form an antibody-antigen complex, wherein the antibody is selected from the group consisting of: an isolated monoclonal antibody comprising a VH domain having the amino acid sequence of SEQ. ID No. 2 and a VL domain having the amino acid sequence of SEQ ID. No. 4 and an isolated monoclonal antibody comprising a VH domain having the amino acid sequence of SEQ. ID No. 6 and a VL domain having the amino acid sequence of SEQ ID. No. 8, wherein the antigen is selected from the group consisting of: IL(interleukin)-1 alpha, IL-1beta, IL-2, IL-7, IL-10, IL-18, IL-36alpha, IL-36beta, IL-36gamma, IL-33, granulocyte-macrophage colony stimulating factor (GM-CSF), interferon-inducible protein 10 (IP10/CXCL10), monocyte chemoattractant protein 1 (MCP1), macrophage inflammatory protein-1-alpha (MIP1A), and tumor necrosis factor-alpha (TNF-alpha);

removing the antibody-antigen complex from the body fluid; and returning the body fluid to the patient.

2. The method of claim 1, further comprising conjugating the antibody-antigen complex with a second antibody.

3. The method of claim 2, wherein the second antibody comprises a moiety that increases the efficacy of removal, thereby forming an antibody-moiety-antigen complex.

4. The method of claim 3, wherein the moiety comprises an iron moiety and further comprises applying a radiofrequency emission to the antigen and the body fluid.

5. The method of claim 1, further comprising determining an efficacy of treatment based on testing the body fluid after the treating the body fluid and before returning the body fluid to the patient.

6. The method of claim 1, wherein the removing of the antibody antigen complex is selected from a group consisting of: a mechanical filter, a chemical filter, a dialysis machine, a molecular filter, molecular adsorbent recirculating system (MARS), and a plasmapheresis unit.

7. The method of claim 1, wherein the body fluid is selected from the group consisting of: blood and cerebrospinal fluid.

8. A device for treating a body fluid extracorporeally of a patient with an inflammatory cytokine storm, comprising:

a first stage including an inlet for the body fluid and at least one exterior wall defining a treatment chamber;

a second stage, fluidly connected to the first stage, comprising a removal module and an outlet for the body fluid, wherein the treatment chamber comprises a delivery tube for introducing a treatment into the treatment chamber, wherein the delivery tube comprises a hollow tube including at least one interior wall defining a plurality of holes through which the treatment can be added to the treatment chamber, wherein the treatment is delivered through the hollow tube in counter-current mode with reference to the body fluid; and the device being configured to:

remove the body fluid from a patient;

apply a treatment to the body fluid, wherein the treatment comprises an antibody that joins with an antigen in the body fluid to form an antibody-antigen complex, wherein the antibody is selected from the group consisting of: an isolated monoclonal antibody comprising a VH domain having the amino acid sequence of SEQ. ID No. 2 and a VL domain having the amino acid sequence of SEQ ID. No. 4 and an isolated monoclonal antibody comprising a VH domain having the amino acid sequence of SEQ. ID No. 6 and a VL domain having the amino acid sequence of SEQ ID. No. 8, wherein the antigen is selected from the group consisting of: IL(interleukin)-1 alpha, IL-1beta, IL-2, IL-7, IL-10, IL-18, IL-36alpha, IL-36beta, IL-36gamma, IL-33, granulocyte-macrophage colony stimulating factor (GM-CSF), interferon-inducible protein 10 (IP10/CXCL10), monocyte chemoattractant protein 1 (MCP1), macrophage inflammatory protein-1-alpha (MIP1A), and tumor necrosis factor-alpha (TNF-alpha); and remove the antibody-antigen complex from the body fluid; and return the body fluid to the patient.

9. The device of claim 8, further comprising conjugating the antibody-antigen complex with a second antibody.

10. The device of claim 9, wherein the second antibody comprises a moiety that increases the efficacy of removal, thereby forming an antibody-moiety-antigen complex.

11. The device of claim 10, wherein the moiety comprises an iron moiety and further comprises applying a radiofrequency emission to the antigen and the body fluid.

12. The device of claim 8, further comprising determining an efficacy of treatment based on testing the body fluid after the treating the body fluid and before returning the body fluid to the patient.

13. The device of claim 8, wherein the removing of the antibody antigen complex is selected from a group consisting of: a mechanical filter, a chemical filter, a dialysis machine, a molecular filter, molecular adsorbent recirculating system (MARS), and a plasmapheresis unit.

14. A product for treating a body fluid extracorporeally of a patient with an inflammatory cytokine storm, comprising:

a first stage including an inlet for the body fluid and at least one exterior wall defining a treatment chamber; and a second stage, fluidly connected to the first stage, comprising a removal module and an outlet for the body fluid, wherein the treatment chamber comprises a delivery tube for introducing a treatment into the treatment chamber, wherein the delivery tube comprises a hollow tube including at least one interior wall defining a plurality of holes through which the treatment can be added to the treatment chamber, wherein the treatment is delivered through the hollow tube in counter-current mode with reference to the body fluid, wherein the treatment comprises an antibody that joins with an antigen in the body fluid to form an antibody-antigen complex, wherein the antibody is selected from the group consisting of: an isolated monoclonal antibody comprising a VH domain having the amino acid sequence of SEQ. ID No. 2 and a VL domain having the amino acid sequence of SEQ ID. No. 4 and an isolated monoclonal antibody comprising a VH domain having the amino acid sequence of SEQ. ID No. 6 and a VL domain having the amino acid sequence of SEQ ID. No. 8, wherein the antigen is selected from the group consisting of: IL(interleukin)-1 alpha, IL-1beta, IL-2, IL-7, IL-10, IL-18, IL-36alpha, IL-36beta, IL-36gamma, IL-33, granulocyte-macrophage colony stimulating factor (GM-CSF), interferon-inducible protein 10 (IP10/CXCL10), monocyte chemoattractant protein 1 (MCP1), macrophage inflammatory protein-1-alpha (MIP1A), and tumor necrosis factor-alpha (TNF-alpha).

* * * * *